(12) United States Patent
Lee et al.

(10) Patent No.: US 11,166,934 B2
(45) Date of Patent: Nov. 9, 2021

(54) PHARMACEUTICAL COMPOSITION FOR PREVENTING OR TREATING ALLERGIC DISEASES SUCH AS ASTHMA OR ATOPY INCLUDING BAICALEIN AS ACTIVE INGREDIENT

(71) Applicant: Azcuris Co., Ltd., Sejong-si (KR)

(72) Inventors: Ki Yong Lee, Sejong (KR); Young Ho Jeon, Sejong (KR); Youngjoo Byun, Daejeon (KR); Kiho Lee, Seoul (KR); Yong Woo Jung, Daejeon (KR)

(73) Assignee: Azcuris Co., Ltd., Sejong-si (KR)

( * ) Notice: Subject to any disclaimer, the term of this patent is extended or adjusted under 35 U.S.C. 154(b) by 0 days.

(21) Appl. No.: 16/473,354

(22) PCT Filed: Jan. 4, 2018

(86) PCT No.: PCT/KR2018/000167
§ 371 (c)(1),
(2) Date: Jun. 25, 2019

(87) PCT Pub. No.: WO2018/128408
PCT Pub. Date: Jul. 12, 2018

(65) Prior Publication Data
US 2020/0121634 A1  Apr. 23, 2020

(30) Foreign Application Priority Data
Jan. 6, 2017  (KR) .................. 10-2017-0002332

(51) Int. Cl.
*A61K 47/34* (2017.01)
*A61K 31/53* (2006.01)
*A61K 31/4184* (2006.01)
*A61K 9/00* (2006.01)
*A61P 33/02* (2006.01)
*A61K 31/352* (2006.01)
*A61K 31/404* (2006.01)
*A61K 31/4745* (2006.01)
*A61K 36/539* (2006.01)

(52) U.S. Cl.
CPC .......... *A61K 31/352* (2013.01); *A61K 31/404* (2013.01); *A61K 31/4745* (2013.01); *A61K 36/539* (2013.01)

(58) Field of Classification Search
CPC ............. A61K 31/352; A61K 31/404; A61K 31/4745; A61K 36/539
See application file for complete search history.

(56) References Cited

FOREIGN PATENT DOCUMENTS

KR 10-2015-0047047 A 5/2015
WO WO 2009/052411 A2 4/2009

OTHER PUBLICATIONS

Mabalirajan et al. in Plos One, vol. 8, Issue 4, e-62916, pp. 1-13 (2013) (Year: 2013).*
Gong et al. in Journal of Nutrition 142:47-56 (2012) (Year: 2012).*
Cianferoni et al. Expert Review of Clinical Immunology 10(11), 1463-1474 (2014) (Abstract). (Year: 2014).*
Extended European Search Report dated Oct. 7, 2020 in counterpart European Patent Application No. 18736717.2 (8 pages in English).
Mabalirajan, Ulaganathan et al., "Baicalein Reduces Airway Injury in Allergen and IL-13 Induced Airway Inflammation", *PloS one*, vol. 8, Issue 4, Apr. 2013 (pp. 1-13).
Kyung Ryu, Eun et al., "Wogonin, a plant flavone from Scutellariae radix, attenuated ovalbumin-induced airway inflammation in mouse model of asthma via the suppression of IL-4/STAT6 signaling", *Journal of Clinical Biochemistry and Nutrition*, vol. 57, No. 2, Sep. 2015 (pp. 105-112).
Sato, Akihiko et al., "High antiallergic activity of 5,6,4'-trihydroxy-7,8,3'-trimethoxyflavone and 5,6-dihydroxy-7,8,3',4'-tetramethoxyflavone from Eau de Cologne mint (Mentha × piperita citrata)", *Fitoterapia*, vol. 102, Apr. 2015 (pp. 74-83).
Bae, Min-Jung, et al. "Baicalein induces CD4+ Foxp3+ T cells and enhances intestinal barrier function in a mouse model of food allergy", *Scientific reports*, vol. 6, 2016, (pp. 1-11).
International Search Report dated Apr. 30, 2018 in counterpart International Patent Application No. PCT/KR2018/000167 (3 pages in English and 3 pages in Korean).

* cited by examiner

*Primary Examiner* — Dennis Heyer
(74) *Attorney, Agent, or Firm* — NSIP Law (57) ABSTRACT

The present invention relates to a pharmaceutical composition for preventing or treating allergic diseases such as asthma or atopy including baicalein as an active ingredient. Baicalein is capable of regulating thymic stromal lymphopoietin-mediated signal transduction. The pharmaceutical composition of the present invention can effectively suppress inflammatory responses of allergic or asthmatic diseases due to the presence of baicalein extracted from Scutellariae Radix that regulates TSLP-mediated intracellular signal transduction to inhibit intracellular phosphorylation of STATS and inhibit the binding of TSLP to TSLPR. In addition, the pharmaceutical composition of the present invention may further include one or more compounds having synergistic effects with baicalein. In this case, the pharmaceutical composition can more effectively suppress inflammatory responses of allergic diseases such as asthma or atopy.

7 Claims, 5 Drawing Sheets

PHARMACEUTICAL COMPOSITION FOR PREVENTING OR TREATING ALLERGIC DISEASES SUCH AS ASTHMA OR ATOPY INCLUDING BAICALEIN AS ACTIVE INGREDIENT

CROSS REFERENCE TO RELATED APPLICATIONS

This application is a U.S. National Stage Application of International Application No. PCT/KR2018/000167, filed on Jan. 4, 2018, which claims the benefit under 35 USC 119(a) and 365(b) of Korean Patent Application No. 10-2017-0002332, filed on Jan. 6, 2017, in the Korean Intellectual Property Office, the entire disclosure of which is incorporated herein by reference for all purposes.

TECHNICAL FIELD

The present invention relates to a pharmaceutical composition for preventing or treating allergic diseases such as asthma or atopy including baicalein as an active ingredient. More specifically, the present invention relates to a pharmaceutical composition for preventing or treating allergic diseases such as asthma or atopy which includes, as an active ingredient, baicalein capable of regulating thymic stromal lymphopoietin-mediated signal transduction.

BACKGROUND ART

The number of patients with asthma, an allergic inflammatory disease, is estimated to be approximately 100 million worldwide. The scale of the global market associated with the treatment of atopic diseases is known to amount to approximately 2 trillion South Korean won. The prevalence of asthma was 10% in the population of elementary school children in South Korea in 2012 according to a 2012 report by the Statistics Korea. In addition, the prevalence of atopy was 20.6% in the pediatric population in South Korea according to a 2012 report by the Korea Centers for Disease Control and Prevention.

Bronchodilators, inhaled steroids, anti-inflammatory agents, etc. are currently available as asthma therapeutics. Steroids are widely used to treat atopy. However, these therapeutic agents are temporarily effective in ameliorating symptoms of allergic diseases but cannot basically control allergic diseases, failing to fundamentally treat the diseases. Further, the therapeutic agents may cause serious side effects.

Allergic inflammatory diseases such as asthma or atopy are known as immune diseases and Th2 cells are estimated to play a pivotal role in causing allergic responses. Th2 cells are produced by differentiation of CD4 cells. When stimulated by an antigen in lymphocytes, CD4 T cells can differentiate into various types of Th cells depending on the type of cytokines recognized by the cells. That is, when a cytokine recognized by CD4 T cells is IL-12, CD4 cells differentiate into Th1 cells. When cytokines recognized by CD4 T cells are type 2 cytokines such as thymic stromal lymphopoietin (TSLP) or IL-4, CD4 cells differentiate into Th2 to cause allergic responses. Other additional Th cells are produced depending on the type of cytokines recognized by CD4 T cells.

Such cytokines include TSLP, IL-25, and IL-33. Among them, TSLP is anticipated to play the most important role in the development of disease. For example, it was found that when the secretion of TSLP in animal models is inhibited, Th2 cells are difficult to produce and activate, causing no disease in the animals. It was also reported that inhibition of TSLP in an animal whose disease progresses leads to the treatment of the disease. Taken together, TSLP is an important cytokine that acts on both the differentiation and activation of Th2 cells and its regulation is recognized to be important in the treatment of allergic diseases.

Many therapeutic approaches targeting TSLP have been reported. For example, several reports disclose antibodies which neutralize human TSLP activity and methods for the treatment of asthma, atopic dermatitis, and allergic rhinitis using the antibodies, and TSLP-specific antibodies and uses thereof in the treatment of inflammation and allergic inflammatory diseases.

Scutellariae Radix is the root of *Scutellaria baicalensis* Georgi belonging to the family Labiatae. Scutellariae Radix is used intact or with periderms removed. Scutellariae Radix grows in the mountains of Siberia, Mongolia, the far eastern regions of Russia, China, Korea, etc. Scutellariae Radix has been used as a traditional material for health supplement foods and herbal medicines such as Saiboku-To to treat inflammation, cancer, and bacterial and viral infections in the respiratory tract and the gastrointestinal tract in Korea, Japan, and China. Saiboku-To contains 10 medicinal herbs, including Scutellariae Radix, and was reported to be effective against bronchial asthma. Saiboku-To is also known to be effective for fever reduction, moisturization, detoxification, cholesterol level and blood pressure reduction, bile secretion stimulation, diuresis, and cathartic evacuation. It was reported that flavonoids such as baicalein, baicalin, and wogonin are major ingredients isolated from Scutellariae Radix.

Various functional compositions based on Scutellariae Radix extracts are known. For example, a Scutellariae Radix extract effective in preventing or treating periodontal diseases or erectile dysfunction or stimulating hair growth or having neuroprotective activity and a pharmaceutical preparation including the Scutellariae Radix extract, a cosmetic composition for alleviating skin inflammation and atopy including a *Laetiporus sulphurous* fermented broth as an active ingredient, and a composition for inhibiting the maturation of dendritic cells including baicalein from Scutellariae Radix have been disclosed in the patent literature. A composition for treating or preventing alcohol-induced neurotoxicity including baicalein as an active ingredient, a composition for preventing or treating hearing loss including baicalein as an active ingredient, a composition for improving cognitive function including baicalein as an active ingredient, and a therapeutic agent for drug abuse including baicalein as an active ingredient are also known in the literature.

However, there has been no report on the activity of baicalein, a physiologically active substance from Scutellariae Radix, for allergy and asthma.

PRIOR ART DOCUMENTS

Non-Patent Document: Homma, M.; Oka, K.; Yamada, T.; Niitsuma, T.; Ihto, H.; Takahashi, N., A strategy for discovering biologically active compounds with high probability in traditional Chinese herb remedies: An application of Saiboku-To in bronchial asthma. *Analytical Biochemistry* 1992, 202 (1), 179-187.

DETAILED DESCRIPTION OF THE INVENTION

Problems to be Solved by the Invention

Thus, the present invention intends to provide a pharmaceutical composition including baicalein as an active ingredient that exhibits outstanding efficacy in preventing or treating allergic diseases such as asthma or atopy due to its ability to regulate intracellular signal transduction mediated by thymic stromal lymphopoietin (TSLP) to effectively inhibit intracellular phosphorylation of STAT5 and inhibit the binding of TSLP to TSLPR.

Means for Solving the Problems

One aspect of the present invention provides a pharmaceutical composition for preventing or treating allergic diseases such as asthma or atopy including, as an active ingredient, baicalein represented by Formula 1:

[Formula 1]

and
a pharmaceutically acceptable carrier.

For superior prophylactic or therapeutic effects on allergic diseases such as asthma or atopy, the pharmaceutical composition of the present invention may further include one or more of the compounds represented by Formulae 2 to 6:

[Formula 2]

[Formula 3]

[Formula 4]

[Formula 5]

[Formula 6]

According to one embodiment of the present invention, the pharmaceutical composition may further include one or more of the compounds represented by Formulae 5 and 6:

[Formula 5]

[Formula 6]

The pharmaceutical composition of the present invention regulates intracellular signal transduction mediated by thymic stromal lymphopoietin (TSLP) to inhibit intracellular phosphorylation of STAT5 and inhibit the binding of TSLP to TSLPR.

Effects of the Invention

The pharmaceutical composition of the present invention can effectively suppress inflammatory responses of allergic diseases such as asthma or atopy due to the presence of baicalein extracted from Scutellariae Radix that regulates TSLP-mediated intracellular signal transduction to inhibit intracellular phosphorylation of STAT5 and inhibit the binding of TSLP to TSLPR.

In addition, the pharmaceutical composition of the present invention can more effectively suppress inflammatory responses of allergic diseases such as asthma or atopy due to the presence of one or more compounds having synergistic effects with baicalein.

BRIEF DESCRIPTION OF THE DRAWINGS

FIGS. 4 to 8 are histograms showing the inhibitions of binding of TSLP to TSLPR, which were measured by ELISA in Experimental Example 2, demonstrating that the binding of TSLP to TSLPR was inhibited by treatment with baicalein of Formula 1 isolated from a Scutellariae Radix extract.

Specifically.

BEST MODE FOR CARRYING OUT THE INVENTION

Figure 1:
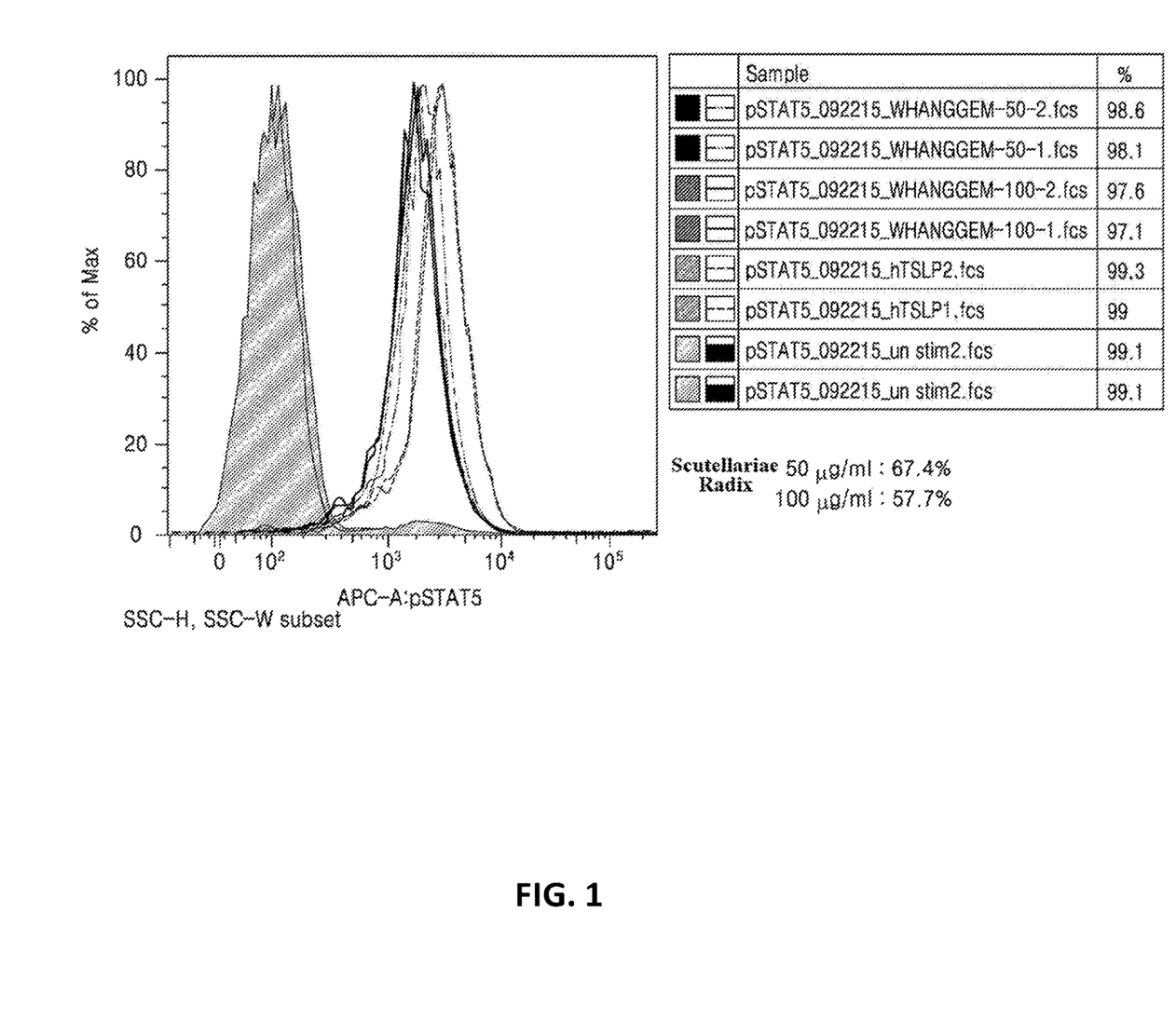
FIG. 1 graphically shows changes in the intracellular phosphorylation of STAT5 molecules when TSLP-mediated intracellular signal transduction was regulated by treatment with a Scutellariae Radix extract in Experimental Example 1.
Figure 2:
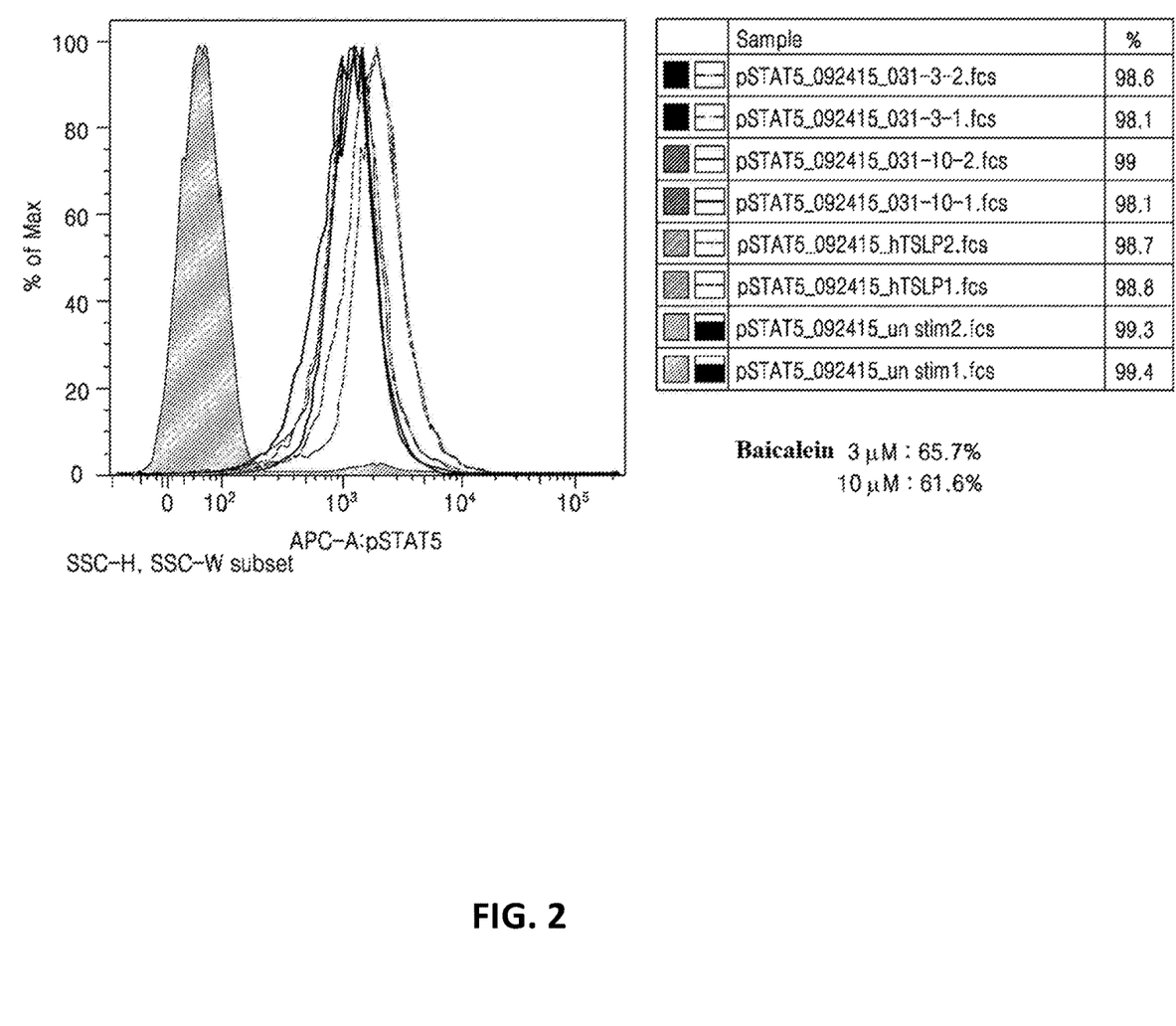
FIG. 2 graphically shows changes in the intracellular phosphorylation of STAT5 molecules when TSLP-mediated intracellular signaling was regulated by treatment with baicalein of Formula 1 isolated from a Scutellariae Radix extract.
Figure 3:
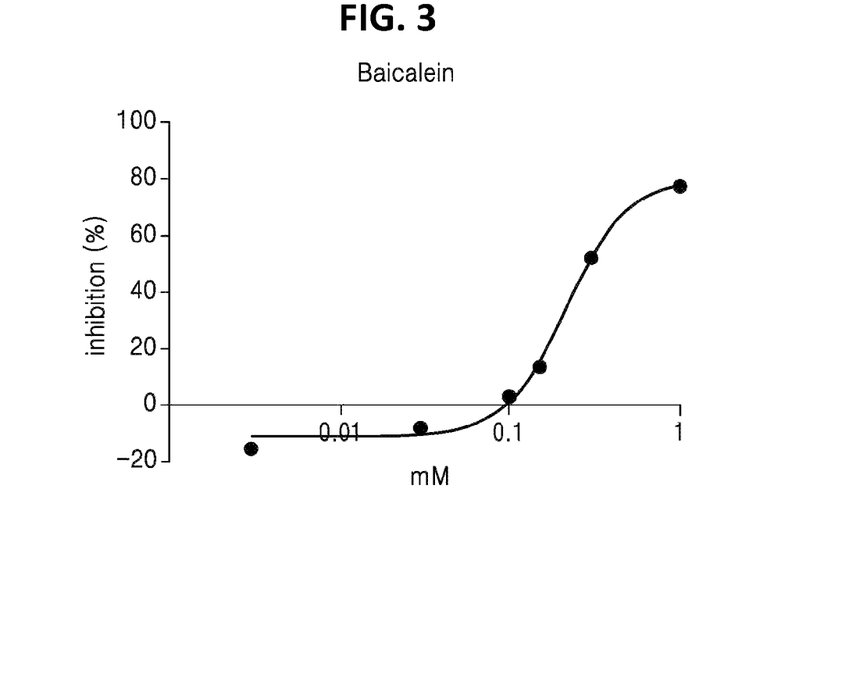
FIG. 3 shows the IC50 value of baicalein of Formula 1 isolated from a Scutellariae Radix extract.
Figure 4:
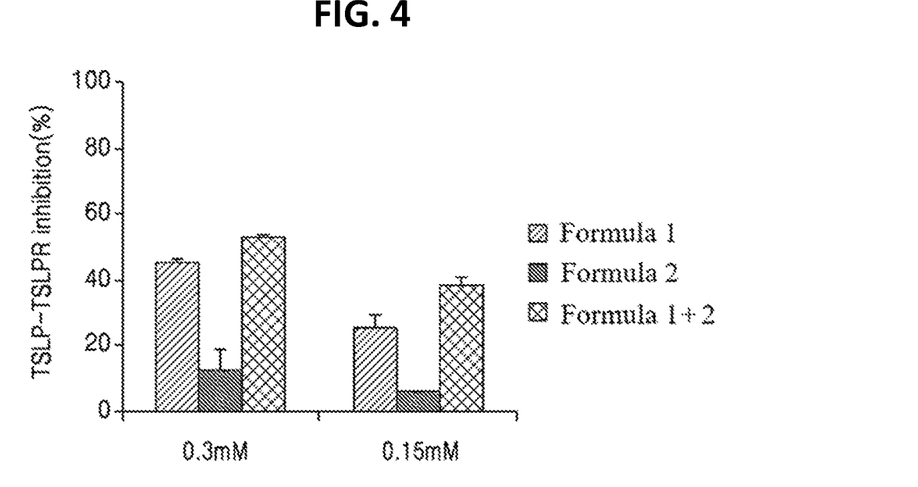
FIG. 4 is a histogram showing the synergistic effect of the flavonoid compound of Formula 2 when treated simultaneously with baicalein.
Figure 5:
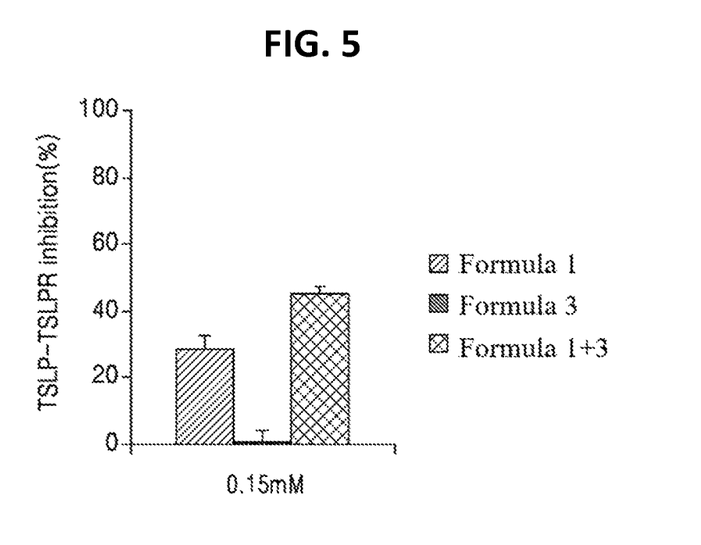
FIG. 5 is a histogram showing the synergistic effect of the flavonoid compound of Formula 3 when treated simultaneously with baicalein.
Figure 6:
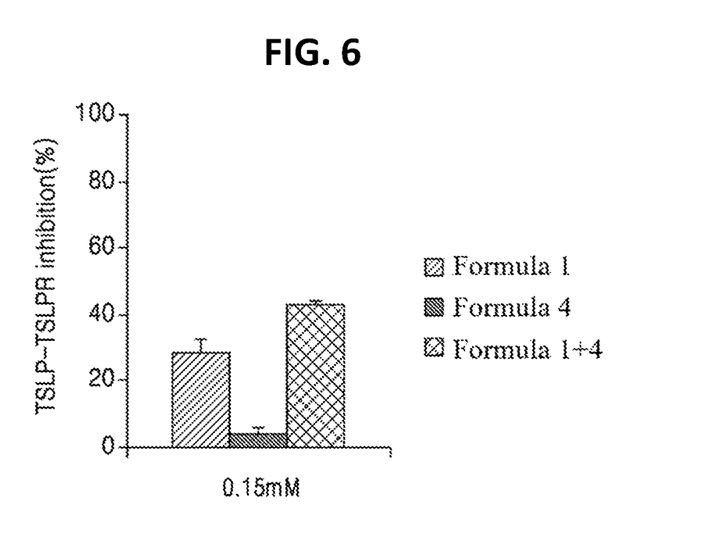
FIG. 6 is a histogram showing the synergistic effect of the dye of Formula 4 isolated from *Persicaria tinctoria* when treated simultaneously with baicalein.
Figure 7:
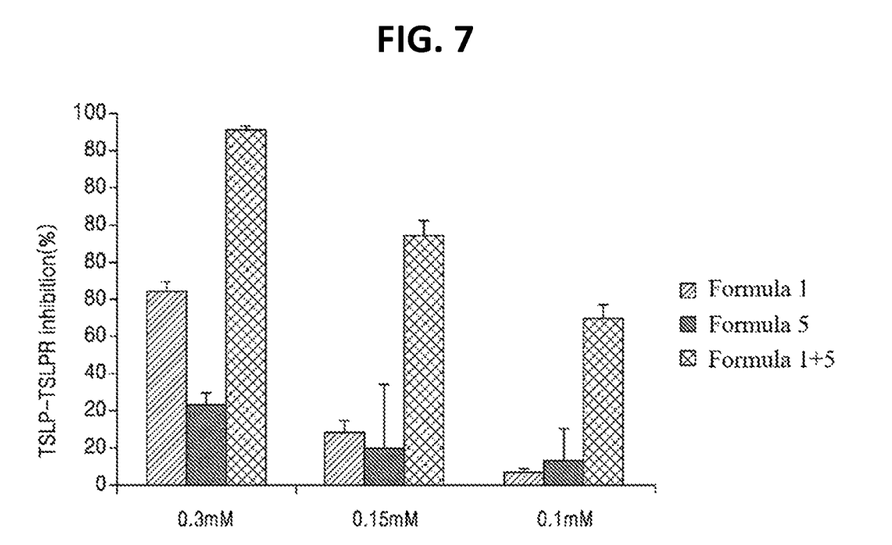
FIG. 7 is a histogram showing the synergistic effect of the synthetic compound of Formula 5 when treated with simultaneously baicalein.
Figure 8:
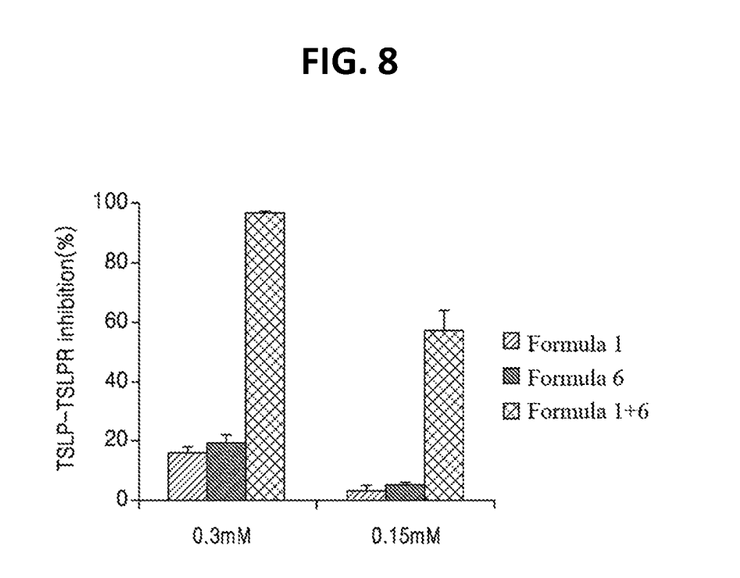
FIG. 8 is a histogram showing the synergistic effect of the synthetic compound of Formula 6 when treated simultaneously with baicalein.

The present invention will now be described in more detail.

In an effort to overcome the disadvantages of currently widely used therapeutic agents, for example, steroids, for asthma or atopy, the inventors of the present invention have conducted research to isolate novel substances from natural sources, and as a result, succeeded in isolating a compound having excellent efficacy in preventing and treating allergic diseases such as asthma or atopy.

The present invention is directed to a pharmaceutical composition for preventing or treating allergic diseases such as asthma or atopy including, as an active ingredient, baicalein isolated from a Scutellariae Radix extract.

The active ingredient baicalein is represented by Formula 1:

[Formula 1]

The pharmaceutical composition of the present invention is characterized by its ability to regulate thymic stromal lymphoprotein (TSLP)-mediated intracellular signal transduction to inhibit intracellular phosphorylation of STAT5 and inhibit the binding of TSLP to TSLPR.

Treatment with a combination of baicalein represented by Formula 1 and one or more of the compounds represented by Formulae 2 to 6 achieves synergistic effects on the prevention or treatment of allergic diseases such as asthma or atopy, which was confirmed in Experimental Example 2.

The compounds of Formulae 2 and 3 are pelargonidin chloride and kaempferol, respectively, which are flavonoid compounds found in plants. The compound of Formula 4 is an indigo dye that can be isolated from *Persicaria tinctoria*. The compounds of Formulae 5 and 6 are 5-(2-(dimethylamino)ethyl)-2-phenyloxazolo[4,5-c]quinolin-4(5H)-one and N,N-dimethyl-2-((2-phenyloxazolo[4,5-c]quinolin4-yl)oxy)ethanamine, respectively.

Accordingly, the pharmaceutical composition of the present invention may further include one or more of the compounds of Formulae 2 to 6.

The pharmaceutical composition of the present invention can be used to prevent and treat a wide range of allergic diseases such as asthma or atopy. Examples of the allergic diseases include, but not limited to, atopic dermatitis, urticarial rhinitis, and allergic rhinitis.

The pharmaceutical composition of the present invention may be complexed with other known drugs for the prevention and treatment of allergic diseases such as asthma or atopy before administration or may further include one or more other additives selected from carriers, diluents, adjuvants, and stabilizers.

The dosage form of the composition according to the present invention may vary depending on the mode of administration desired. Examples of such dosage forms include, but not limited to, solid, semi-solid, and liquid formulations, such as tablets, pills, powders, capsules, gels, ointments, emulsions, and suspensions. The composition of the present invention may be administered in unit dosage forms suitable for single administration of precise dosages. The composition of the present invention may be administered orally or parenterally. For parenteral administration, the composition of the present invention may be administered intravenously, subcutaneously or intramuscularly.

Depending on the formulation desired, the composition may further include one or more pharmaceutically acceptable carriers, diluents, adjuvants, and stabilizers, which are defined as aqueous-based vehicles commonly used to formulate pharmaceutical compositions for human administration.

The term "carrier" means a substance that facilitates the incorporation of a compound into cells or tissues. Examples of suitable carriers include, but not limited to, carbohydrate-based compounds, such as lactose, amylose, dextrose, sucrose, sorbitol, mannitol, starch, and cellulose, gum acacia, calcium phosphate, alginate, gelatin, calcium silicate, microcrystalline cellulose, polyvinylpyrrolidone, cellulose, water, syrups, salt solutions, alcohols, gum Arabic, vegetable oils, such as corn oil, cotton seed oil, soybean oil, olive oil, and coconut oil, polyethylene glycol, methyl cellulose, methyl hydroxybenzoate, propyl hydroxybenzoate, talc, magnesium stearate, and mineral oils, which are commonly used to formulate pharmaceutical compositions. The term "diluent" is defined as a substance diluted in water that can dissolve the compound of interest as well as stabilize the biologically active form of the compound. Examples of suitable diluents include distilled water, physiological saline, Ringer's solution, dextrose solution, and Hank's solution. The stabilizers can be selected from the group consisting of proteins, carbohydrates, buffers, and mixtures thereof. The composition of the present invention may optionally further include one or more additives. Examples of such optional additives include, but not limited to, lubricating agents, wetting agents, sweetening agents, flavoring agents, emulsifying agents, suspending agents, and preservatives.

Such additional additives as carriers, diluents, adjuvants, and stabilizers may be used in amounts effective to acquire pharmaceutically acceptable formulations in view of the solubility, biological activity, and other characteristics of the active ingredient.

As used herein, the term "prevent" or "preventing" refers to inhibiting a disease or disorder from occurring in an animal or human that may be predisposed to the disease or disorder but has not yet been diagnosed as having it. As used herein, the term "treat" or "treating" refers to inhibiting the development of a disease or disorder or ameliorating or eliminating the disease or disorder.

As used herein, the term "including as an active ingredient" means the presence of the corresponding ingredient in an amount necessary or sufficient to achieve a desired biological effect. In real applications, the active ingredient is used in a therapeutically effective amount to treat a target disease and such an amount can suitably be determined taking into consideration other toxicities caused by the active ingredient. For example, the amount of the active ingredient may vary depending on various factors, such as the disease or condition to be treated, the dosage form of the composition, the size of a subject or the severity of the disease or condition. The effective amount of the composition can be empirically determined by those skilled in the art without excessive experiments.

By "pharmaceutically acceptable" is meant that the biological activity and properties of the compound are not impaired.

Other terms and abbreviations used herein may be understood as their meanings recognized generally by those skilled in the art, unless otherwise defined.

Mode for Carrying Out the Invention

The present invention will be explained in more detail with reference to the following examples. These examples are provided to assist in understanding the invention and are not intended to limit the scope of the invention.

Example 1

Isolation and Purification of the Inventive Compound (Formula 1) from Scutellariae Radix Extract and Structural Determination of the Compound Scutellariae Radix (1.5 kg) was cut into pieces, extracted three times with 80% methanol (for 1 h each), filtered, and concentrated under reduced pressure. The methanol extract was suspended in water, fractionated with hexane (n-$C_6H_{12}$), ethyl acetate ($C_4H_8O_2$), and water-saturated butanol ($C_4H_9OH$). The ethyl acetate fraction was separated by silica gel column chromatography with increasing polarity and recrystallized to give the compound of Formula 1 as a yellow powder.

[Formula 1]

Subsequently, the physicochemical properties and spectroscopic properties of the compound of Formula 1 were investigated. The results are as follows.

(1) Molecular formula: $C_{15}H_{10}O_4$
(2) Appearance: Yellow amorphous powder
(3) ESI-MS (m/z) (negative mode): 269.05 [M-H]$^-$
(4) Proton nuclear magnetic resonance spectrum $^1$H-NMR (300 MHz, $CD_3OD$) δ 6.77 (1H, s, H-8), 6.98 (1H, s, H-3), 7.68 (3H, m, J=1.5 Hz, H-3, 4', 5'), 8.12 (2H, m, J=1.5 Hz, H-2', 6'), 12.07 (1H, s, 5-OH)
(5) Carbon nuclear magnetic resonance spectrum $^{13}$C-NMR (75 MHz, $CD_3OD$) δ 95.89 (C-8), 106.20 (C-3), 106.70 (C-10), 128.20 (C-2', 6'), 131.03 (C-3', 5'), 131.57 (C-6), 133.74 (C-1'), 133.84 (C-4'), 148.75 (C-5), 153.00 (C-9), 155.74 (C-7), 166.41 (C-2), 185.05 (C-4)

The above physicochemical data were compared with the literature values, and as a result, the compound of Formula 1 was identified as baicalein.

EXPERIMENTAL EXAMPLE 1

Cell-Based Efficacy Evaluation Using FACS

The binding of TSLP to TSLP receptor activates various signaling pathways, mainly the JAK/STAT pathway. TSLP-mediated signaling is well known to specifically phosphorylate STAT5 among STAT molecules. In order to confirm whether the inventive compound effectively inhibits the binding of TSLP to TSLP receptor, it is necessary to determine the degree of phosphorylation of STAT5 molecules in the JAK/STAT pathway activated by this binding. When the inventive compound effectively inhibits the binding of TSLP to TSLPR, the level of phosphorylation of STAT5 molecules can be inhibited.

In this example, this fact was confirmed through the following experiment.

First, HMC-1, a human mast cell line, was cultured until an appropriate number of cells were maintained in a 96-well plate. After the supernatant was discarded, mixtures of TSLP (100 ng/mL) and different concentrations (0.3, 3, and 30 μM) of each of the Scutellariae Radix extract and the inventive compound (Formula 1) were treated on cells for 30 min. Cells were fixed with Cytofix. Subsequently, cells were permeabilized with a permeabilization buffer and stained with anti-pSTAT5 antibody at 4° C. for 30 min. Cells were washed three times with the same buffer and analyzed by flow cytometry. After the Scutellariae Radix extract and the compound (Formula 1) isolated from Scutellariae Radix were added, the degrees of intracellular phosphorylation of STAT5 molecule were measured and compared with those in a control treated with TSLP alone. The results are shown in Table 1. The intracellular phosphorylation of STAT5 molecules in the control was 100%.

TABLE 1

| Compound | Degrees of intracellular phosphorylation of STAT5 molecules (%) | |
| --- | --- | --- |
|  | 3 μM | 10 μM |
| Scutellariae Radix extract | 67.4[1] | 57.7[2] |
| Formula 1 | 65.7 | 61.6 |

[1] 50 μg/mL
[2] 100 μg/mL

As can be seen from the results in Table 1, the Scutellariae Radix extract and the inventive compound (Formula 1) inhibited the binding of TSLP to TSLP receptor to inhibit the phosphorylation of STAT5 molecules, demonstrating their efficacy in inhibiting the binding of TSLP to TSLP receptor.

EXPERIMENTAL EXAMPLE 2

Evaluation of Inhibition of Interaction Between TSLP and TSLPR by ELISA

In this example, an investigation was made as to whether the inventive compound directly inhibits the binding of TSLP to TSLP receptor. To this end, home-made FLAG-TSLP protein and TSLPR-His protein was used to establish an ELISA-based TSLP-TSLPR interaction assay for measuring reactions with HRP. The inhibitory activity of the inventive compound was evaluated by the interaction assay.

The IC50 of baicalein (Formula 1) as an active ingredient isolated from Scutellariae Radix was 215.8 μM. The synergistic effects of baicalein of Formula 1 with the flavonoid compound (pelargonidin chloride) of Formula 2, the flavonoid compound (kaempferol) of Formula 3, the compound (indigo dye) of Formula 4, the synthetic compound of Formula 5, and the synthetic compound of Formula 6 were investigated.

TABLE 2

| Compound | TSLP-TSLPR inhibitions (%) | |
| --- | --- | --- |
|  | 0.3 mM | 0.15 mM |
| Formula 1 | 45.8 ± 0.7 | 25.5 ± 4.0 |
| Formula 2 | 13.1 ± 5.8 | 6.3 ± 0.1 |
| Formula 1 + Formula 2 | 52.7 ± 1.1 | 38.4 ± 2.8 |

TABLE 3

| Compound | TSLP-TSLPR inhibitions (%) 0.15 mM |
| --- | --- |
| Formula 1 | 28.6 ± 4.1 |
| Formula 3 | 0.6 ± 3.7 |
| Formula 1 + Formula 3 | 45.1 ± 2.5 |

TABLE 4

| Compound | TSLP-TSLPR inhibitions (%) 0.15 mM |
| --- | --- |
| Formula 1 | 28.6 ± 4.1 |
| Formula 4 | 3.5 ± 2.7 |
| Formula 1 + Formula 4 | 42.9 ± 1.5 |

TABLE 5

| Compound | TSLP-TSLPR inhibitions (%) | | |
| --- | --- | --- | --- |
|  | 0.3 mM | 0.15 mM | 0.1 mM |
| Formula 1 | 52.5 ± 2.3 | 14.0 ± 3.5 | 3.2 ± 1.3 |
| Formula 5 | 21.6 ± 3.4 | 10.2 ± 17.0 | 6.5 ± 8.6 |
| Formula 1 + Formula 5 | 95.8 ± 1.1 | 67.2 ± 4.1 | 44.8 ± 3.7 |

TABLE 6

| Compound | TSLP-TSLPR inhibitions (%) | |
| --- | --- | --- |
|  | 0.3 mM | 0.15 mM |
| Formula 1 | 16.5 ± 1.6 | 3.5 ± 1.9 |
| Formula 6 | 19.3 ± 3.0 | 5.4 ± 0.7 |
| Formula 1 + Formula 6 | 96.7 ± 0.6 | 57.7 ± 6.5 |

Particularly, insignificant inhibitory effects on the binding of TSLP to TSLP receptor were observed when treated with the compound of Formula 5 or 6 alone, but inhibitions close to 100% were observed at high concentrations when treated with combinations of the compound of Formula 1 and the compound of Formula 5 or 6. These results demonstrate significant synergistic effects of the compound of Formula 1 with the compound of Formulae 5 and 6.

INDUSTRIAL APPLICABILITY

Taken together, the above results indicate that the composition of the present invention can effectively inhibit TSLP, a key cytokine inducing allergic and asthmatic diseases, from binding to TSLP receptor. In conclusion, the composition of the present invention can be used to fundamentally prevent and treat allergic and asthmatic diseases due to its ability to inhibit TSLP-mediated signal transduction.

The invention claimed is:

1. A pharmaceutical composition for treating an allergic disease comprising, as an active ingredient, baicalein represented by Formula 1:

[Formula 1]

;

one or more of the compounds represented by Formulae 5 and 6:

[Formula 5]

[Formula 6]

;

and a pharmaceutically acceptable carrier.

2. The pharmaceutical composition according to claim 1, further comprising one or more of the compounds represented by Formulae 2 and 3:

[Formula 2]

[Formula 3]

.

3. The pharmaceutical composition according to claim 1, wherein the composition regulates intracellular signal transduction mediated by thymic stromal lymphopoietin (TSLP) to inhibit intracellular phosphorylation of STAT5.

4. The pharmaceutical composition according to claim 1, wherein the composition inhibits the binding of thymic stromal lymphopoietin (TSLP) to TSLP receptor.

5. The pharmaceutical composition according to claim 1, wherein the allergic disease is atopic dermatitis, urticarial rhinitis, allergic rhinitis or asthmatic disease.

6. The pharmaceutical composition according to claim 1, wherein the baicalein represented by Formula 1 is extracted from Scutellariae Radix.

7. The pharmaceutical composition according to claim 1, further comprising the compound represented by Formula 4:

[Formula 4]

.

* * * * *